United States Patent [19]
Ghaffari

[11] Patent Number: 5,344,418
[45] Date of Patent: Sep. 6, 1994

[54] OPTICAL SYSTEM FOR TREATMENT OF VASCULAR LESIONS

[76] Inventor: Shahriar Ghaffari, 13091 Pond Springs Rd., Bldg. C, Austin, Tex. 78729-7139

[21] Appl. No.: 807,055

[22] Filed: Dec. 12, 1991

[51] Int. Cl.$^5$ .............................................. A61N 5/06
[52] U.S. Cl. ..................................... 606/9; 606/13; 607/89
[58] Field of Search ................. 128/395–398, 128/783, 804; 606/9–17, 27, 28, 29, 30, 31, 32, 33, 34, 41, 46; 604/289, 21, 22

[56]  References Cited
U.S. PATENT DOCUMENTS

| | | | |
|---|---|---|---|
| 3,693,623 | 9/1972 | Harte et al. | 606/9 |
| 3,821,510 | 6/1974 | Muncheryan | 128/395 |
| 4,316,467 | 2/1982 | Muckerheide | 606/9 |
| 4,733,660 | 3/1988 | Itzkan | 606/17 |
| 5,050,597 | 9/1991 | Daikuzono | 606/10 |
| 5,057,104 | 10/1991 | Chess | 606/9 |
| 5,071,417 | 12/1991 | Sinofsky | 128/398 |
| 5,112,328 | 5/1992 | Taboada | 606/4 |

Primary Examiner—Stephen C. Pellegrino
Assistant Examiner—M. Peffley
Attorney, Agent, or Firm—Gambrell, Wilson & Hamilton

[57] ABSTRACT

An improved optical system for treatment of disorders of the skin, especially vascular lesions, such as PortWine Stains. The system irradiates the skin with radiation at a predetermined wavelength and cools the skin during a predetermined time interval in coordination with delivery of the radiation. The absorption of the radiation by the skin and the change in temperature of the skin is monitored by the system and the operation of the radiation delivery system is controlled to optimize treatment of the vascular lesion. The source of irradiation is an arc lamp and the cooling system delivers a cooling gas to a lens in contact with the skin. The cooling gas can be carbon dioxide, freon, or any other appropriate gas. The lens used has a high heat conductivity and may be formed of sapphire.

8 Claims, 11 Drawing Sheets

OPTICAL SYSTEM FOR TREATMENT OF VASCULAR LESIONS

FIELD OF THE INVENTION

The present invention relates to an optical system for treatment of disorders of the skin, especially vascular lesions, such as Port Wine Stains.

BACKGROUND

PortWine Stains (PWS) are congenital disorders of the skin in which vascular malformations produce red-colored isolated lesions occurring most commonly on the face, trunk and neck. The lesion is basically an area of localized enlarged and ectatic blood vessels in the upper dermis. PWS tends to progress from a pale pink and flat lesions in childhood to nodular and dark red-purple lesions in adulthood. Its unpleasant cosmetic appearance causes psychological stress and makes the patient seek medical help. The goal of PWS treatment is to restore the normal color of the skin by selectively destroying the enlarged blood vessels while keeping the rest of the cutaneous structures intact.

The prior art method of choice for treatment of PWS is photocoagulation of the enlarged blood vessels. Ideally, absorption of the laser light by hemoglobin increases the temperature of the abnormal blood vessels until coagulation of blood and vessel walls takes place. Wavelengths for treatment of PWS are usually selected because of their high absorption by hemoglobin. The argon laser with lines at 488 and 514.4 nm has been selected for treatment of PWS because of its high absorption in blood. Recently better coupling has been achieved by matching a pulse dye laser to the 577 nm peak of oxygenated hemoglobin. However, coagulation of the enlarged vessels has been demonstrated at other wavelengths such as 1.06 and 10.6 $\mu$m.

Ideally, laser treatment should selectively destroy dermal blood vessels up to a depth of approximately 0.6 mm without causing damage to the epidermis, and especially to the epidermal-dermal layer since damage to this layer disturbs the healing process and may lead to scarring. Epidermal melanin, however, is also an important chromophore with strong absorption in the ultraviolet that decreases through the visible spectrum. Melanin, therefore, has been a potential barrier for the incident laser light causing hearing of the epidermis and reducing the amount of light which reaches the underlying blood vessels.

One of the most recent lasers for the treatment of PortWine Stain is the pulsed dye laser tuned to 577 nm, which is at one of the high absorption peaks of hemoglobin. At 577 nm absorption by epidermal melanin and scattering by the dermis is lower than at the 540 nm peak or at argon wavelengths. The rate of heat generation is higher in the blood vessels than in the epidermis. Although pulse durations of 1 $\mu$s or less cause microvascular hemorrhage, 360 $\mu$s pulses seem to be very effective in causing selective vascular damage without excessive damage to the epidermis or non-vascular dermal structure. Although investigators report no scarring or any apparent epidermal damage after treatment of PWS lesions with 360 $\mu$s pulse 577 nm dye laser, at a dose of 6.5 to 10 J/cm$^2$, only an overall lightening of 42% has been obtained in the PWS lesions after the initial treatment, and retreatment sessions improved the overall lightening to 68%. Higher energy doses per treatment may produce unwanted epidermal or dermal damage.

A pulsed dye laser system is expensive for an average Dermatologist with a limited purchasing power. However, in the treatment of vascular lesions the coherence of the laser beam is not a critical consideration as long as a light source with proper powers at the right wavelengths can be focused onto the skin with spot sizes in the range of 3–5 mm in diameter (similar to the spot sizes reported in such applications).

The tunable dye laser based systems have been very effective in exploring the mechanisms of the PWS treatments. At the present, the purchasing cost of such laser based systems is approximately $150,000 and the annual maintenance is estimated to be $25,000 per laser system. Consequently, most Dermatologists can not justify the high cost of purchasing a laser based systems for this application. Another cost consideration is the patients who may not be able to afford the high costs of such treatments. Therefore, there is a need for a low-cost system to achieve the same treatment for a much lower cost than the present treatment cost. Such a system is provided by the present invention, described in greater detail below.

SUMMARY OF THE INVENTION

The present invention provides an improved optical system for treatment of disorders of the skin, especially vascular lesions, such as PortWine Stains. In the preferred embodiment of the present invention the system comprises means for irradiating the skin with radiation at a predetermined wavelength. The system also comprises means for cooling the skin during a predetermined time interval in coordination with delivery of the radiation. The absorption of the radiation by the skin and the change in temperature of the skin is monitored by the system and the operation of the radiation delivery system is controlled to optimize treatment of the vascular lesion. In the preferred embodiment of the invention, the source of irradiation is an arc lamp. The means for cooling comprises a system for delivering a cooling gas to a lens in contact with the skin. The cooling gas can be carbon dioxide, freon, or any other appropriate gas. The lens used in the preferred embodiment is formed of sapphire.

BRIEF DESCRIPTION OF THE DRAWINGS

Further advantages and a more complete understanding of the invention can be obtained by referring to the following detailed description of specific embodiments when taken in conjunction with the accompanying drawings in which.

DETAILED DESCRIPTION OF THE PREFERRED EMBODIMENT

Figure 1:
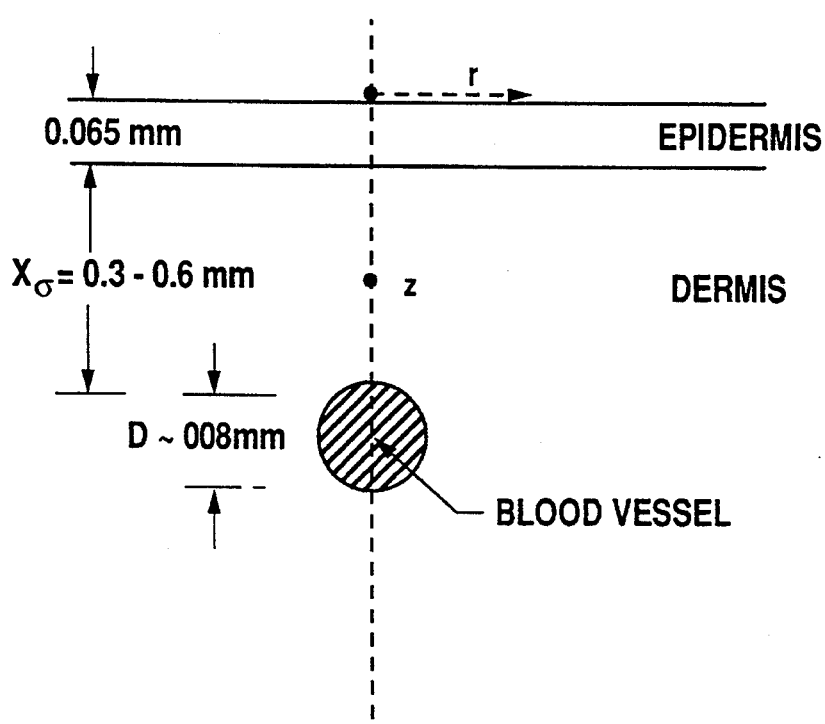
FIG. 1 is an illustration of a blood vessel in relation to the dermis and epidermis.

Optically, the skin can be represented by two layers: a thin absorbing layer (epidermis) and predominantly scattering layer (dermis), as shown in FIG. 1. The enlarged blood vessels in PWS are located mainly at a distance of 0.3 to 0.6 mm from the epidermal-dermal junction. Blood vessels are typically modeled as either a thin absorbing layer or as individual cylinders or spheres. The goal of PWS treatment is to restore the normal color of the skin by selectively destroying the enlarged blood vessels while keeping the rest of the cutaneous structures intact.

Figure 2:
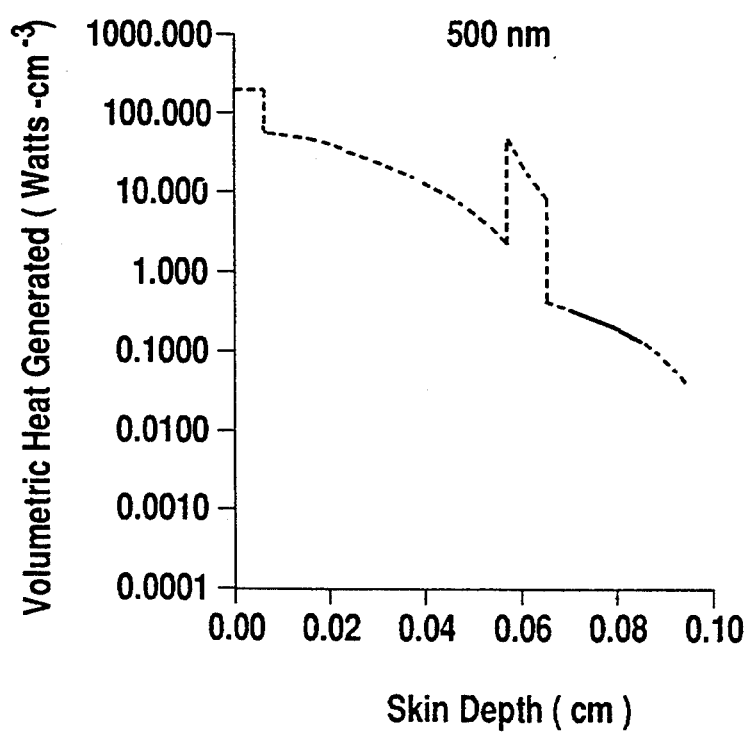
FIG. 2 is a graphical illustration of the volumetric heat generated in skin as a function of depth for 500 nm light.

The rate of heat generation $S[W/cm^3]$ in the tissue due to absorption of radiation is:

$$S(z) = \mu_{a(z)} \phi(z)$$

where $\mu_a$ is the local absorption coefficient and $\phi(z)$ is the fluence rate. The rate of heat generation at 500 nm is shown in FIG. 2.

Figure 3:
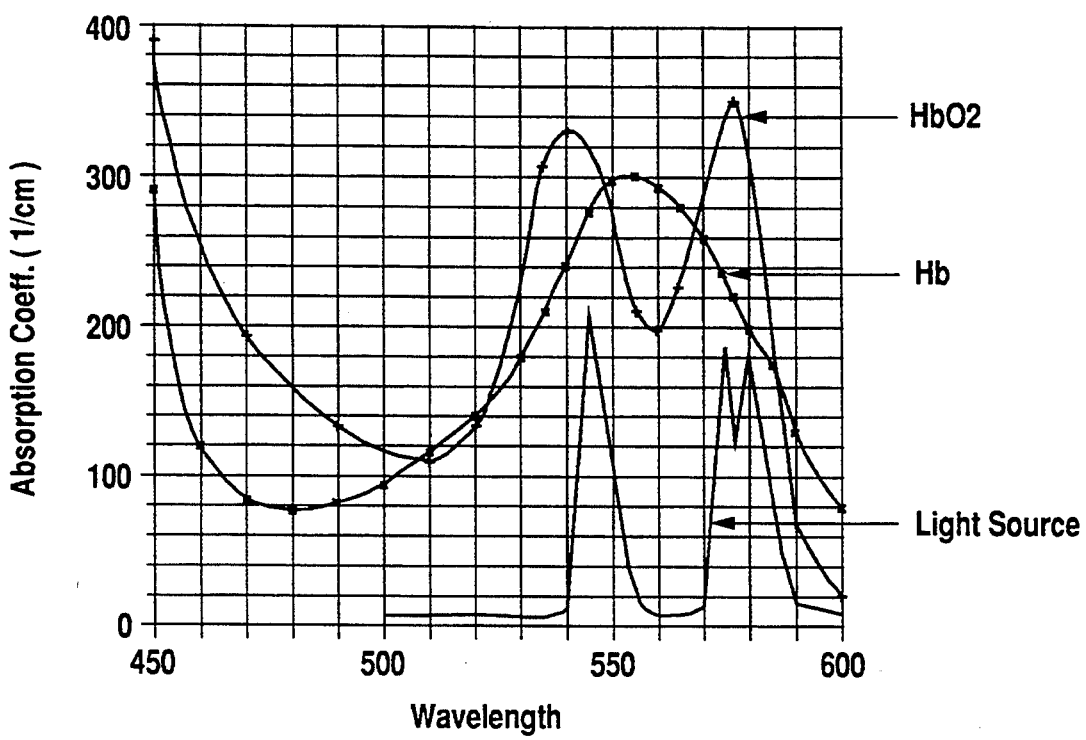
FIG. 3 is a graphical illustration of the absorption of light produce by an arc lamp by blood.

The wavelength spectrum of lasers presently used for PWS treatment vary from 488 nm up to 590 nm with the optimum treatment at 585 nm. FIG. 3, which is the blood absorption characteristic as a function of wavelength, reveals that the absorption of blood (HbO and Hb) is not sharp in a small neighborhood of the selected laser wavelengths. The advantage of using a dye laser at 585 nm appears to be the higher penetration depths with minimal epidermal heating and scarring. It has been suggested that an argon laser would perform better if the heat could be removed from the surface.

Figure 4:
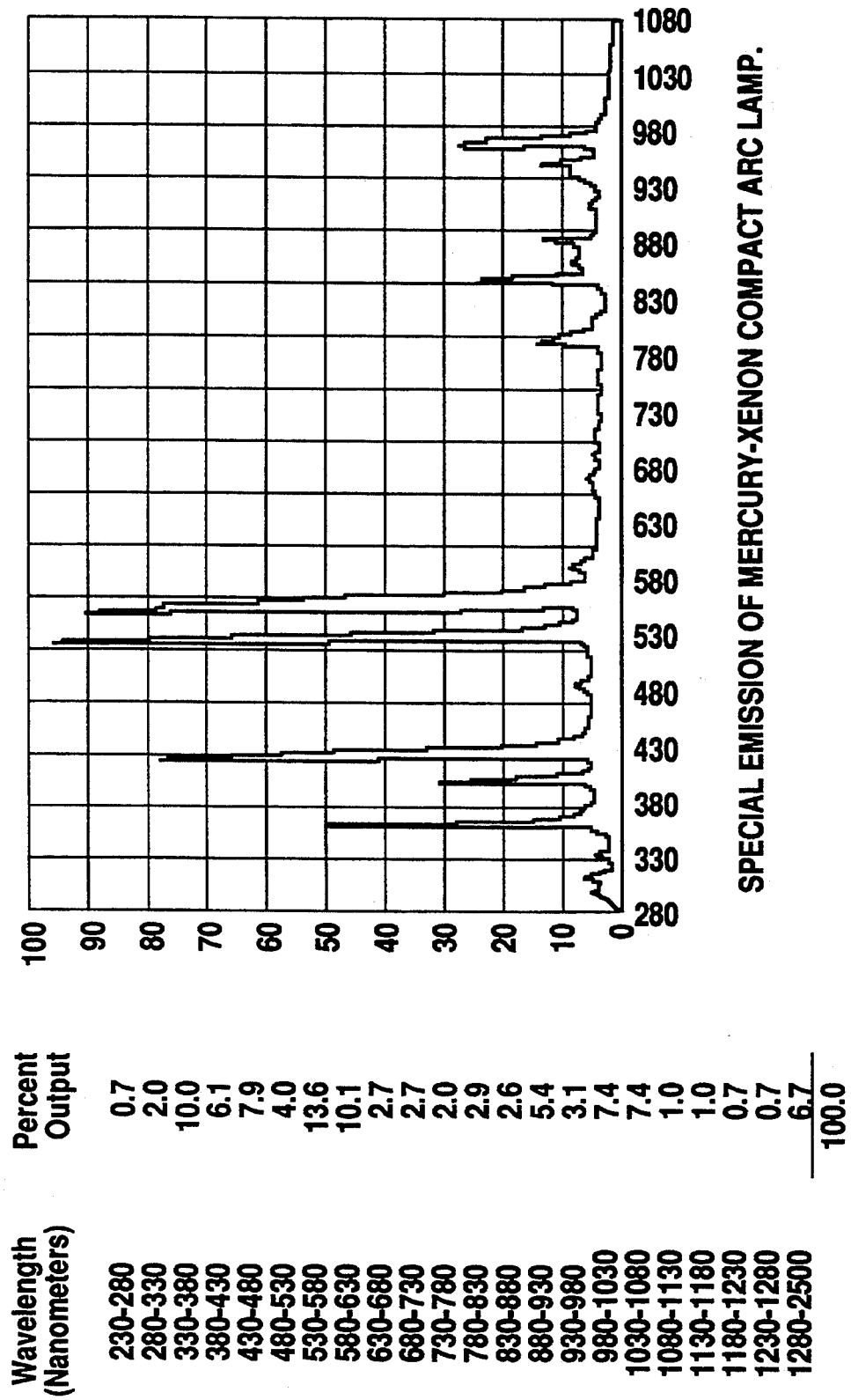
FIG. 4 is a graphical illustration of the spectral emission of a Mercury-Xenon arc lamp.

The light source employed in the present invention is a "Mercury Vapor Arc lamp" with a wavelength characteristic shown in FIG. 4. However, other light sources may be utilized, such as a xenon arc lamp. Arc lamp power ratings up to 10,000 watts are commercially available. However, an Arc lamp with a power rating of 2500 watts would produce sufficient light intensity for vascular lesion treatments. An important characteristic of the lamp is that it produces two narrow linewidths of light about the peaks of 546 and 579 nm, which coincide with blood absorption peaks at 540 and 577 nm. The lamp spectral distribution with respect to the blood absorption spectrum is shown in FIG. 3. The Full Width Half Maximum (FWHM) of the lamp peak at 579 is 10 nm and at 546 is 6 nm.

If the entire band of wavelengths from 530 to 560 nm is used (using the Arc lamp) then the epidermal temperature may exceed the temperature of blood vessels deeper than 0.28 mm. Consequently, the present invention includes a temperature compensation and monitoring system, discussed in greater detail below, to reduce the epidermal and dermal temperatures such that the overall system produces, in the epidermis and dermis, temperatures at least as low as the dye lasers at 577 or 585 nm.

EFFECT OF NARROW-BAND ARC LAMP ON SKIN

Figure 5:
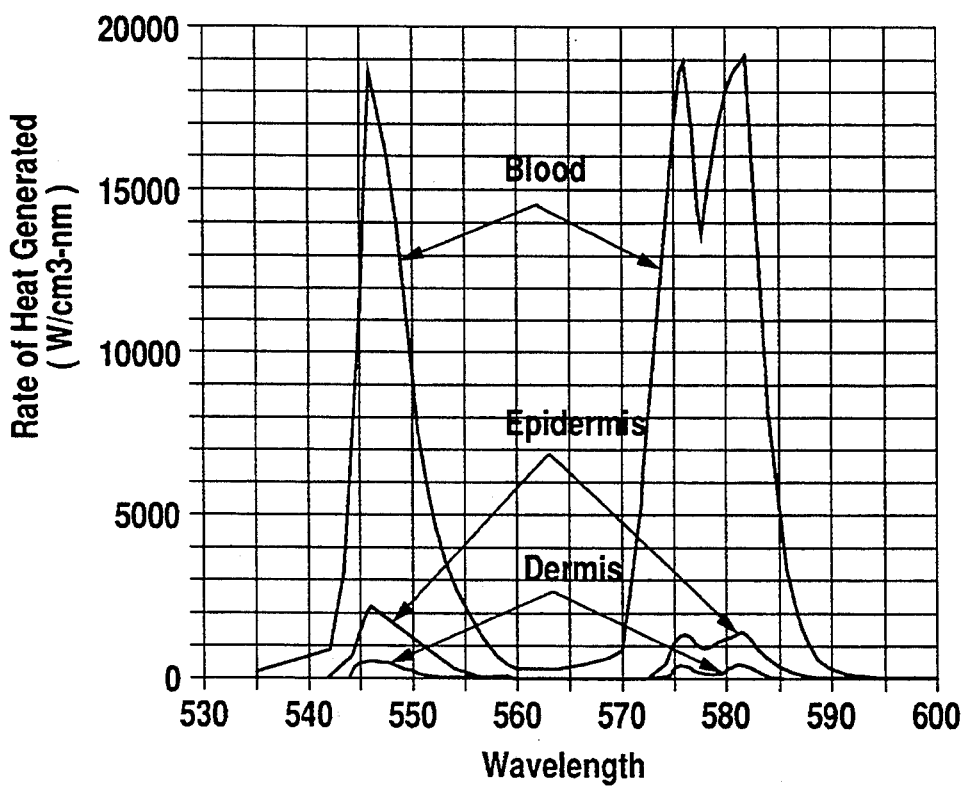
FIG. 5 is a graphical illustration the rate of heat generation as a function of wavelength of irradiation for blood, dermis and epidermis.

FIG. 3 is the blood absorption coefficient in the range of 450–600 nm with the corresponding characteristic of the Arc lamp spectrum. The resultant rate of heat generation in blood, epidermis and dermis are shown in FIG. 5.

Figure 6:
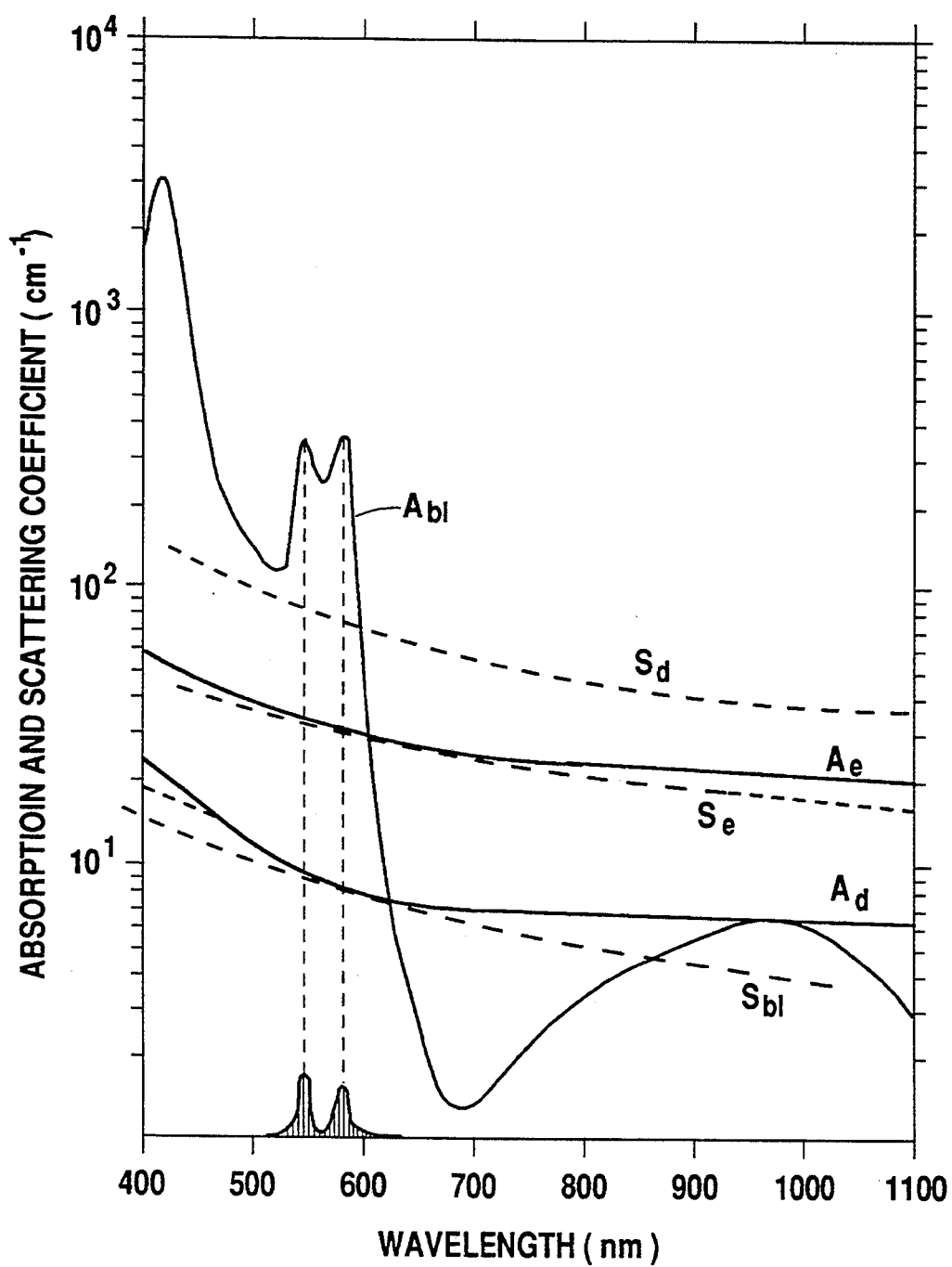
FIG. 6 is a graphical illustration of skin absorption and scattering characteristics.

The difference in the rate of heat generation in the epidermis and dermis for Arc lamp irradiation will result in higher temperatures as compared to the dye laser at 577 and 585 nm at equal irradiance. Since the epidermal heat generation is approximately 3.5 times that of dermis, the dermis will always be at lower temperatures than epidermis. As a result, the temperature of epidermis must be lowered during the Arc lamp irradiation to remove the excess heat generated. The worst case heating of the epidermis is the case of using only 500 nm irradiation. The absorption coefficients at 500 nm, using FIG. 6, are: $A_b = 140$ and $A_e = 38$, $A_d = 12 \text{ cm}^{-1}$. Therefore, the expected temperature in epidermis is 1.72 times more than the case for the dye lasers at 577 and 585 nm (1.36 times higher irradiance @ 1.26 times higher absorption).

The epidermal temperature increase using a dye laser is assumed to be approximately 20° C. In order to achieve an equivalent blood vessel coagulation at 0.6 mm depths using 500 nm, the epidermis temperature must be brought down approximately 15° C. below the normal skin temperature, before irradiation. This is the worst case situation in using the Arc lamp. The system of the present invention is capable of cooling the skin to temperatures as low as 5° C., which is more than the cooling capability needed for this treatment.

Figure 7A:
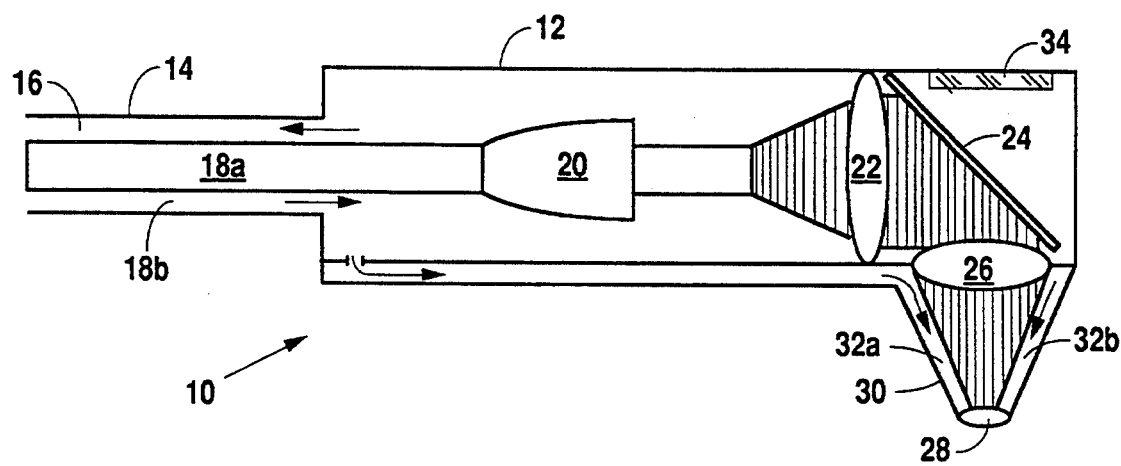
FIGS. 7a–7b is an illustration of the preferred embodiment of the system for delivering radiation to the skin in accordance with the present invention.
Figure 7B:
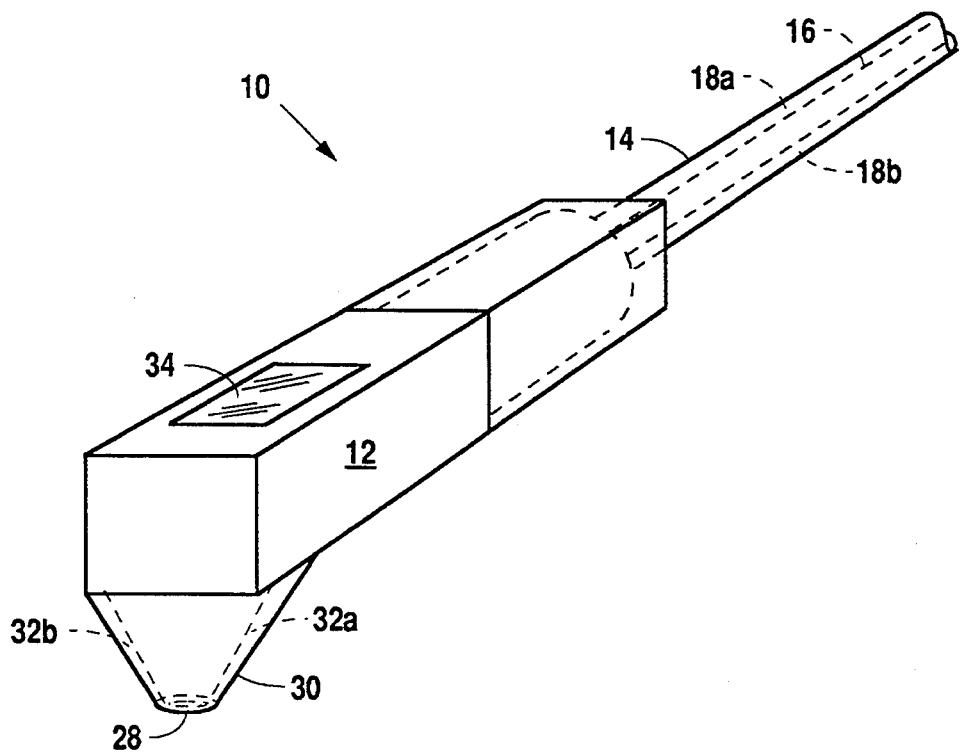

The system show in FIGS. 7a–7b and the alternate embodiment shown in FIGS. 8a–8d is used to deliver light energy to skin while controlling the amount of radiation delivered. Referring to FIG. 7a, the delivery device 10 comprises a housing 12 containing optic components and a cable 14 comprising a fiber bundle 16 and gas channels 18a and 18b for transporting gas to and from the interior of the housing 12. A fiber terminator 20 directs light carried by the fiber bundle 16 toward a primary lens 22. The light passed by the primary lens 22 is reflected by the dichroic mirror 24 toward a secondary mirror 26 which passes the light to a sapphire lens 28 contained in the tip of a conical housing 30. The conical housing includes channels 32a and 32b for transporting cooling gas to the sapphire lens 28. The sapphire lens 28 is placed in contact with the surface of the skin to be treated. The sapphire lens will be cooled by $CO_2$ gas (or freon) flowing around the fiber tip and the lens 28 via the channels 18a, 18b and 32a, 32b, as shown in FIG. 7a. The $CO_2$ may be replaced with freon if desired. A viewing window 34 in the top of the housing can be used to observe the interaction of the radiation with the skin to monitor the progress of the treatment.

Figure 8A:
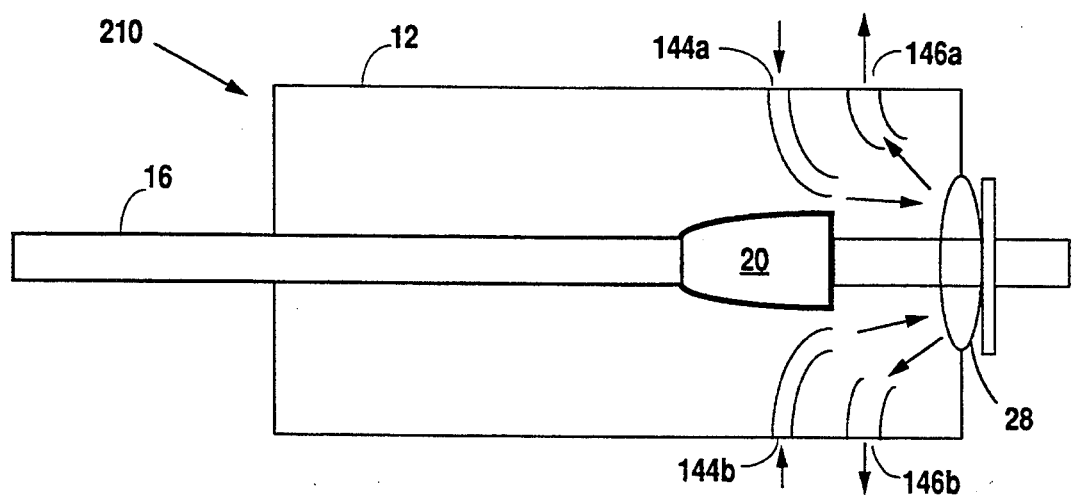
FIGS. 8a–8d is an illustration of alternate embodiments of the system for delivering radiation to the skin in accordance with the present invention.

Referring now to FIGS. 8a–8d, an alternate embodiment of the invention is shown. Elements that are identical to the elements appearing in FIGS. 7a–7b are designated with the same reference numbers for simplicity. As shown in FIG. 8a, delivery device 210 comprises a housing 12 comprising a fiber bundle 16 as well as various optic components. The fiber bundle 16 provides light energy or electromagnetic radiation to fiber terminator 20 which in turn directs the light carried by the fiber bundle 16 to a sapphire lens 28. The sapphire lens 28 produces a collimated beam of light which is then applied to the skin as shown. The delivery device 210 further includes gas flow ports 144a, 144b, 146a and 146b as shown. The gas ports 144a and 144b receive a cooling gas which enters into the housing and then comes in contact with the sapphire lens 28 as shown. After making this contact, the gas then exits from the gas ports 146a and 146b as shown.

Figure 8B:
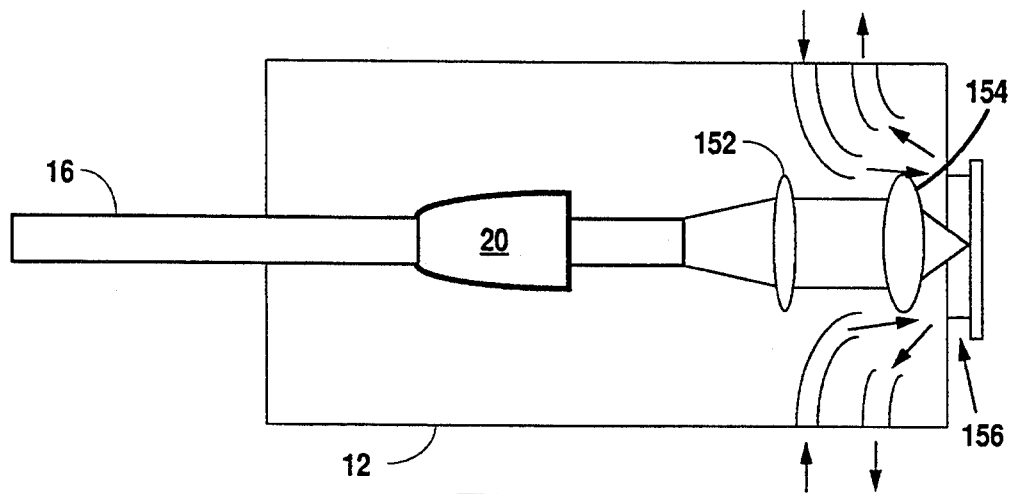

The embodiment of delivery device 212 shown in FIG. 8b is essentially similar except that the light carried by the fiber bundle 16 is passed through a first lens 152 and then to a second lens 154 which focuses the beam through a sapphire window 156 as shown onto the skin.

Figure 8C:
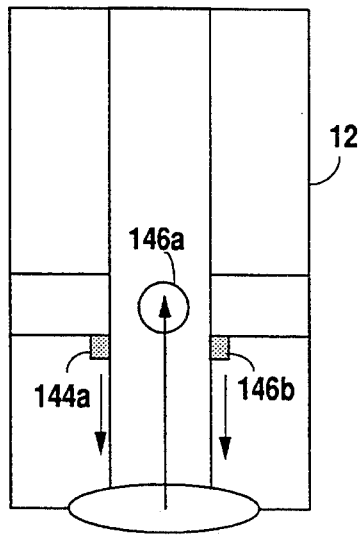
Figure 8D:
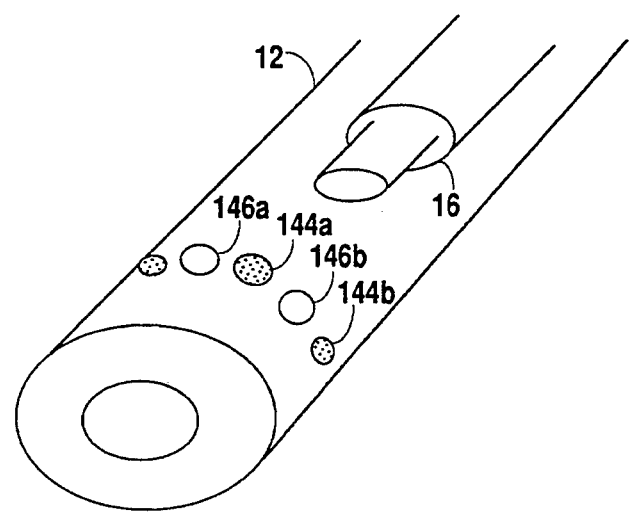

FIG. 8d illustrates the gas flow ports on the outside of the housing 12. Gas ports 144a and 144b are shaded to reflect that gas flow is into the device, and gas ports 146a and 146b are unshaded to reflect that gas exits these ports. As shown in FIG. 8d, the housing 12 may contain any number, i.e. more than four, gas flow ports.

FIG. 8c illustrates the gas flow pattern of the device 210. As shown, the gas flow ports 144a and 144b receive gas from outside of the housing and direct this gas toward the sapphire lens 28. The gas comes in contact with the sapphire lens 28 and then passes outside one of the gas flow exit ports, for example, gas flow port 146a.

Figure 9:
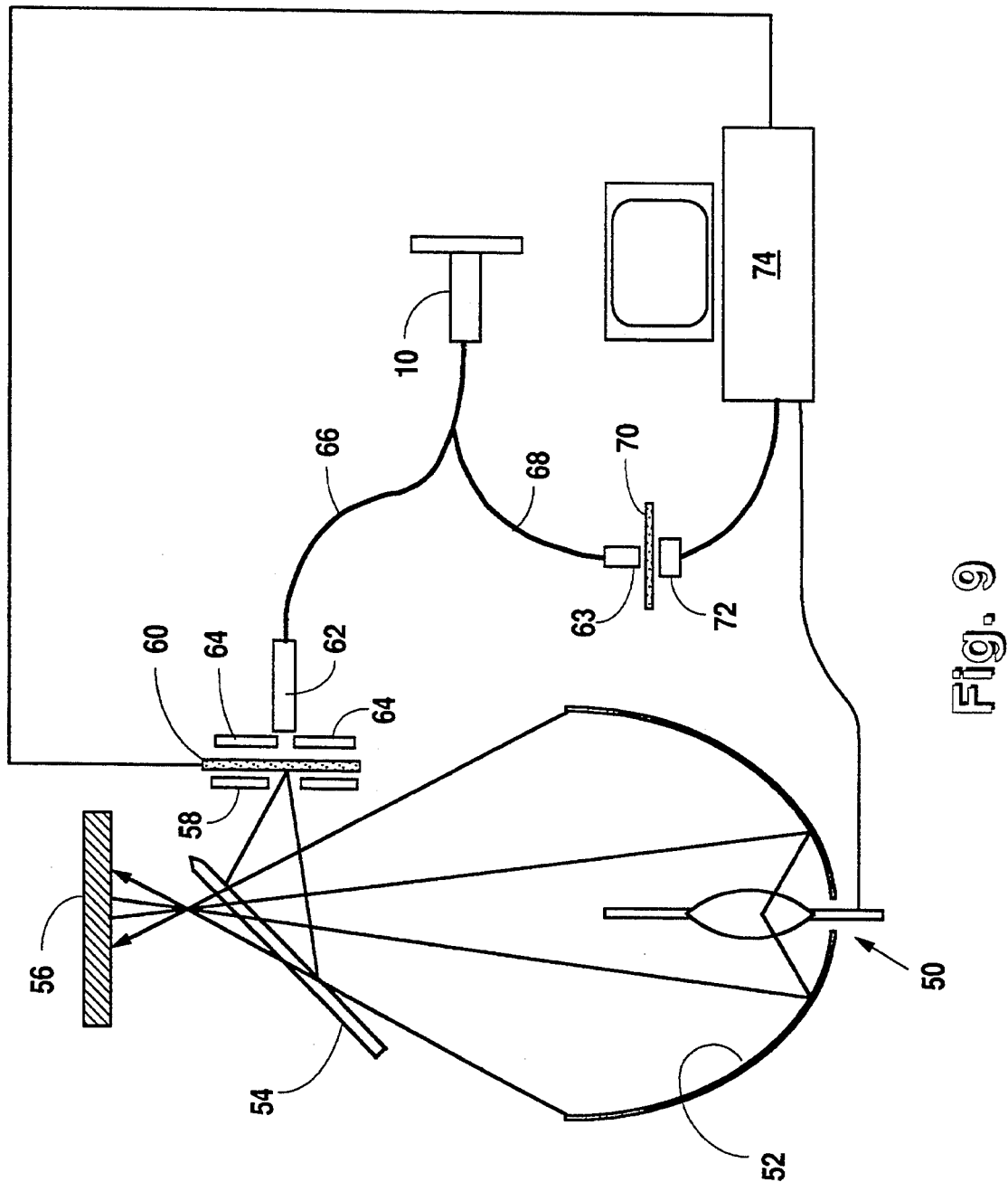
FIG. 9 is an illustration of a computer based control system for controlling the rate of irradiation of the treatment area.

FIG. 9 shows a system wherein the components discussed above are used in connection with a computer to monitor and control the operation of the optical delivery system. The light produced by an arc lamp 50 is focused by a reflector 52 and directed toward a "cold" mirror 54. The cold mirror is a dichroic mirror which passes 90% of the infrared radiation produced by the arc lamp 50 and thus reflecting only approximately 10% of the infrared light. A heat sink 56 absorbs the infrared light passed by the cold mirror 54. The light which is reflected by the cold mirror passes through a shutter 58 and a dichroic filter 60 to be received by a fiber optic terminator 62 secured to a mirror 64. It is not necessary for the filter 60 to be capable of absorbing large amounts of infrared radiation, since the infrared has been effectively removed by passing through the cold mirror 54. The light received by the terminator 62 is transmitted via fiber bundle 66 to the delivery system 10. Light reflected by the skin is transmitted via cable 68 to a reflection monitoring system comprising a filter 70 and a detector 72, which produces an output signal corresponding to the intensity and wavelength of the reflected light. The computer 74 which is used as the feedback controller, directly controls the shutter 58 between the light source and the fiber tip. Output irradiance of the system may be controlled by using built-in tables stored in the computer memory for different irradiation parameters. The specific surface temperature and irradiation parameters may also be preset by the operator through the computer 74.

Figure 14A:
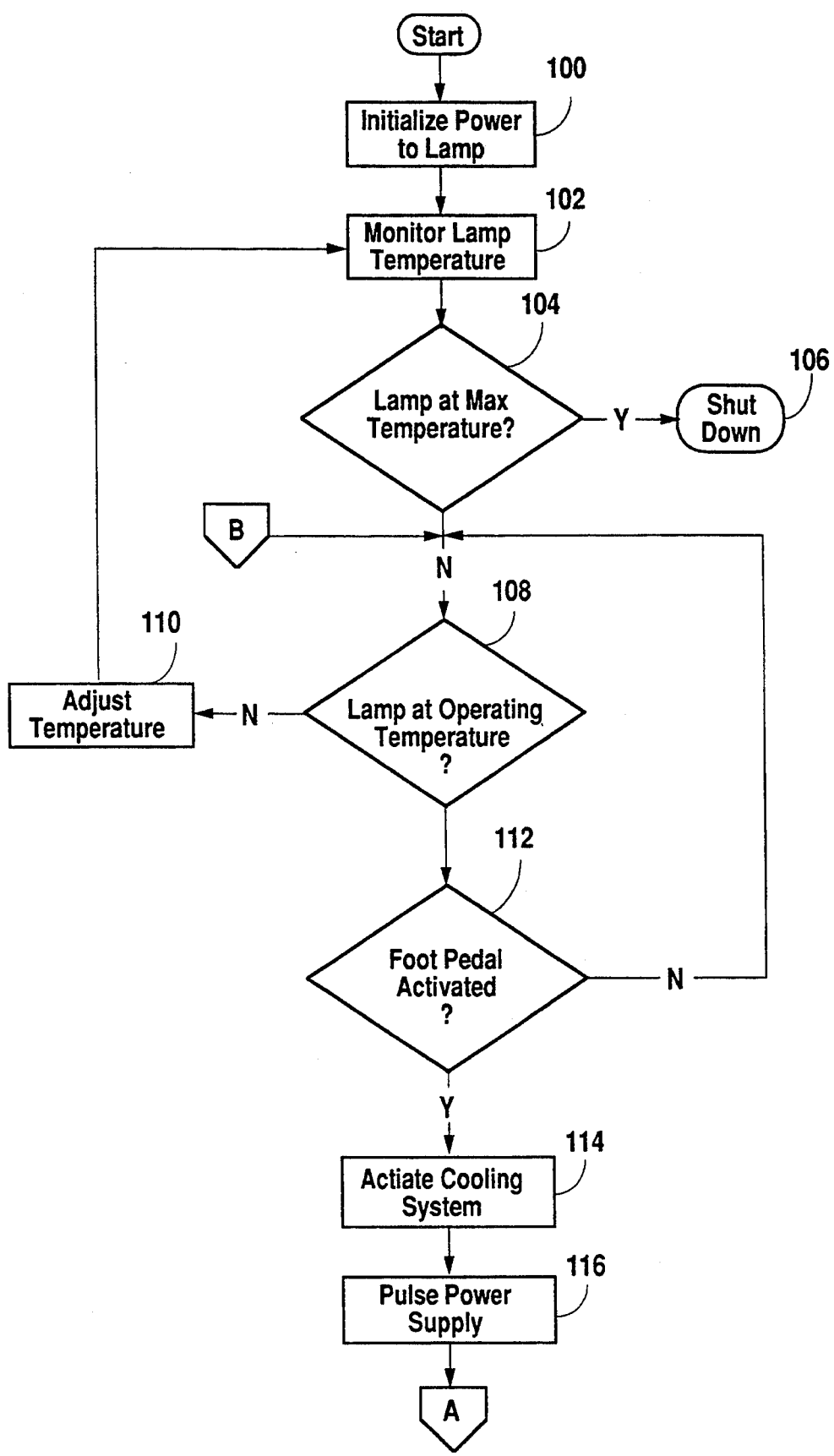
FIGS. 14a–14b are flow charts of the control and processing steps implemented in the system of the present invention.
Figure 14B:
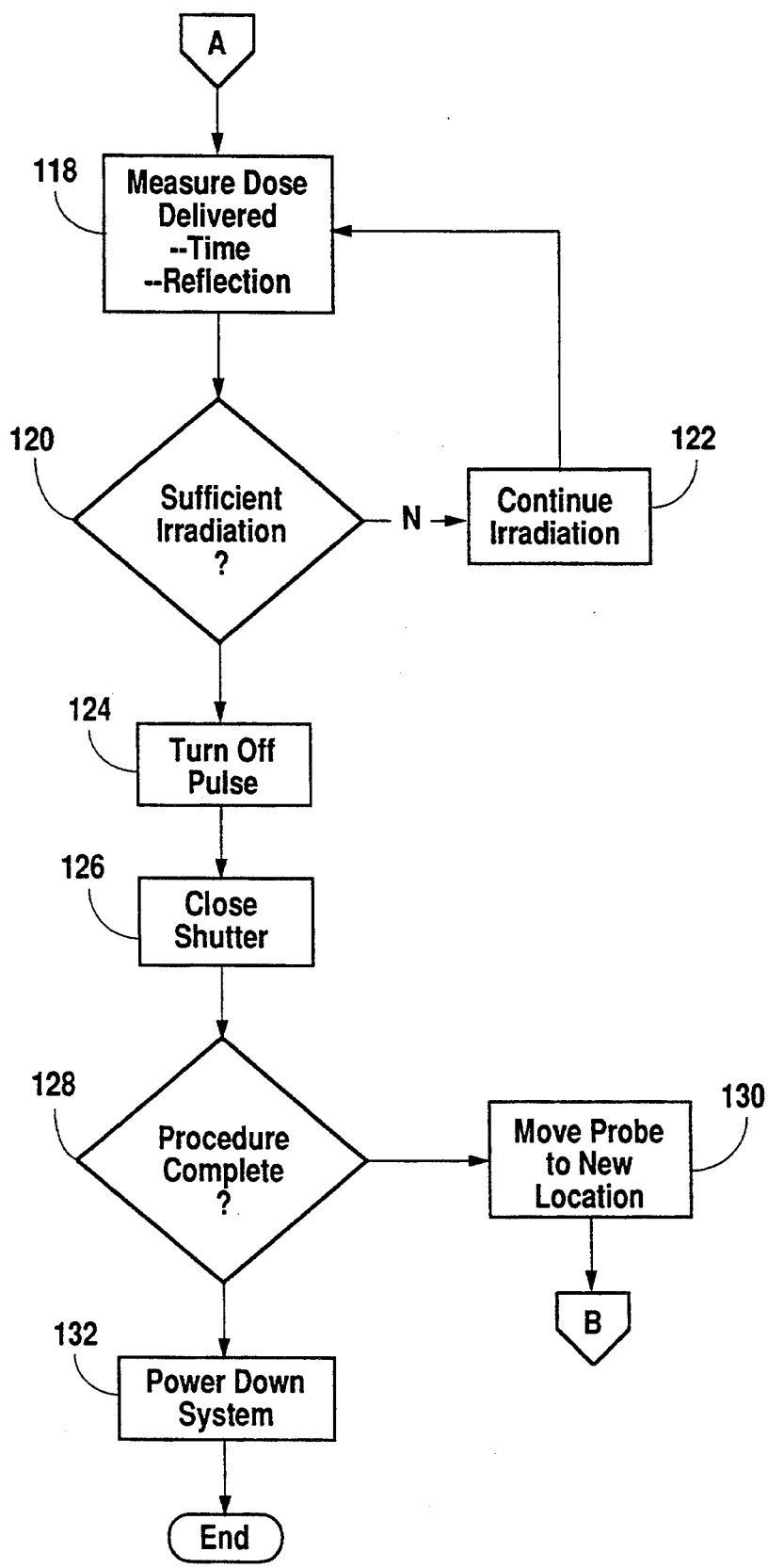

FIGS. 14a and 14b illustrate the processing steps to control the system of the present invention. In step 100 the power to the lamp is initialized and in step 102 the temperature of the lamp is monitored. In step 104, a determination is made of whether the lamp is at the maximum temperature. If the lamp is at the maximum temperature, then the system is shut down in step 106. However, if the lamp is not at the maximum temperature, then a determination is made in step 108 of whether the lamp is at operating temperature. If the lamp is not at operating temperature, then the temperature is adjusted in step 110 and the system returns to step 102. However, if the lamp is at the operating temperature, then the system proceeds to step 112 where a determination is made of whether the foot pedal switch is activated. If the foot pedal is not activated, the system returns to step 108. However, if the foot pedal is activated, the cooling system is activated in step 114 and the power supply is pulsed in step 116. In step 118, the dose of radiation delivered to the skin is measured using two methods—time of delivery and reflection of radiation by the skin. In step 120 a decision is made of whether sufficient radiation has been delivered to the skin. If sufficient radiation has not been delivered, then the system continues to deliver radiation in step 122. However, if sufficient radiation has been delivered, then the pulse is turned off in step 124 and the shutter is closed in step 124. In step 128, a decision is made of whether the procedure is complete. If the procedure is not complete, the probe is moved to a new location and the system proceeds to step 108. However, if the procedure is complete, the system is powered down in step 132.

SURFACE COOLING DURING LIGHT IRRADIATION

Prior investigators have reported that cooling the skin with ice packs prior to treatment of PortWine Stains with argon laser radiation decreased the incidence of scarring. Other investigators, using Neodymium-YAG laser, also reported reduced damage to the epidermis by skin-cooling techniques using direct spraying of freon during laser irradiation. Other reports further suggest that varying skin temperature has an effect on the dose required to produce purpura in human skin with a pulse tunable dye laser.

The surface cooling over a long period of time (i.e. hundreds of seconds) causes blood vessel reactions. The small blood vessels (i.e. less than 100–150 microns) will be shut down if the cooling of the skin is continued for several minutes. After prolonged cooling of the skin at temperatures below 15° C., the blood vessels enlarge. Previous data indicate a sudden change in blood flow as the blood vessel temperature is decreased below approximately 15° C.

Figure 10:
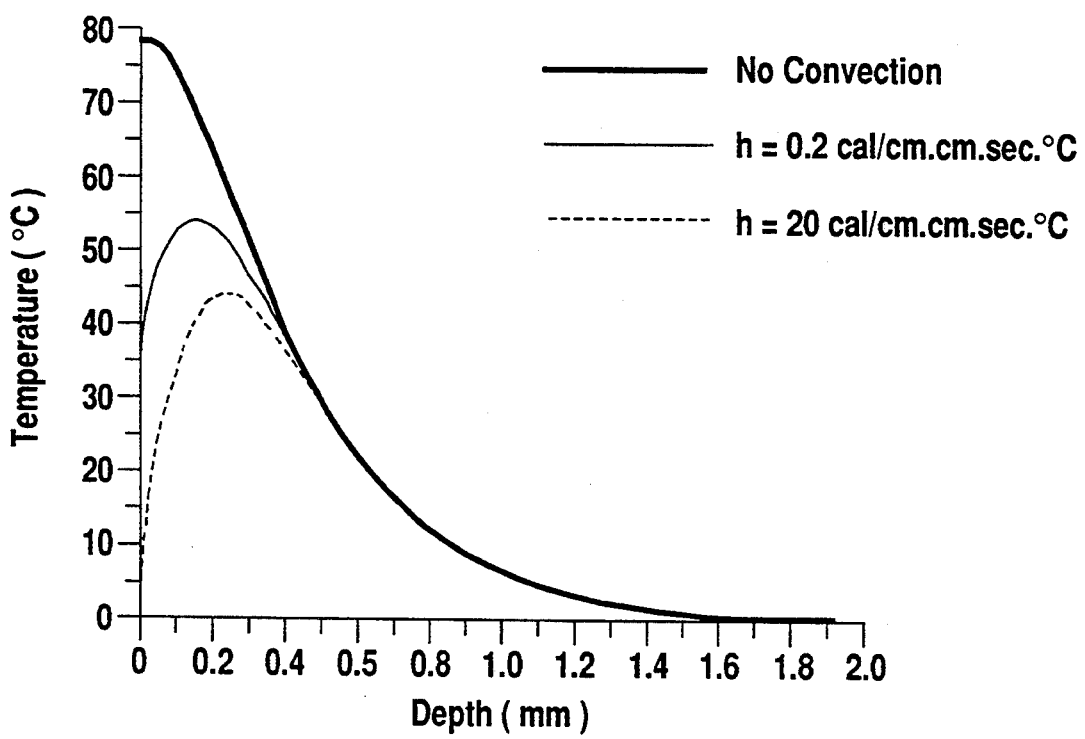
FIG. 10 is a graphical illustration of the effects of cooling on skin.

The advantage of controlled epidermal surface cooling during irradiation is the lower temperature of the epidermis. The main consideration in cooling the skin surface is the cooling rate which must be controlled for a near ideal treatment. The surface cooling effect for the case of a simple thick medium (with tissue parameters, i.e. Absorption=23 $cm^{-1}$, Scattering=10 $cm^{-1}$) irradiated with 2 W, 2 mm Argon laser beam for 250 millisecond, has been simulated on a computer and the results are shown in FIG. 10. The curves for several cases from no-cooling up to a large convective cooling are shown in FIG. 10. The curves due to surface cooling clearly indicate a much lower temperature at the surface than that of the non-cooling curve. Surface cooling may cause the maximum temperature to move away from the surface.

Figure 11:
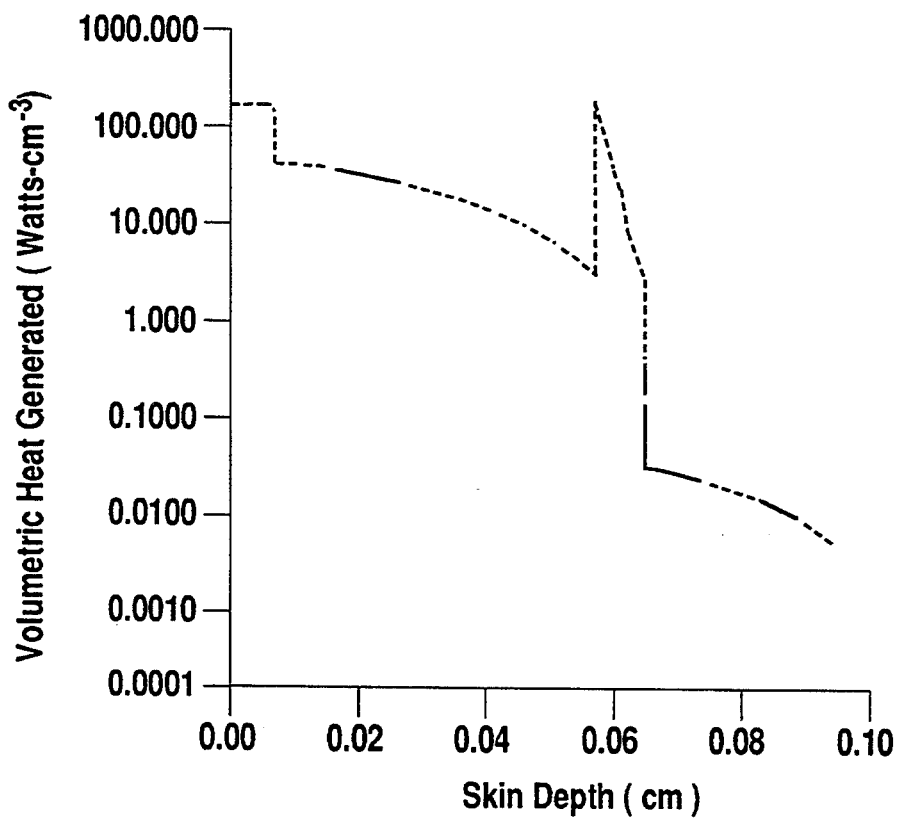
FIG. 11 is a graphical illustration of volumetric heat generated in skin as a function of depth for irradiation at 577 nm.

FIGS. 2 and 11 are the expected rate of heat generation as a function of depth in skin for wavelengths of 500 nm and 577 nm. These curves are based on one-dimensional diffusion theory and should represent the rate of heat generation at the center of a 3-5 mm spot. Considering both cases of FIG. 2 and FIG. 11, it may be concluded that the maximum depth to which the blood vessels are destroyed, at any wavelength, is the depth that the temperature of the blood vessels is equal to the temperature of epidermis. For example, the maximum depth that the dye laser may destroy the blood vessels at 577 nm case (FIG. 11 ) is approximately 0.6 mm whereas at the same depth the 500 nm wavelength does not produce as much temperature due to its lower blood absorption coefficient.

Figure 12:
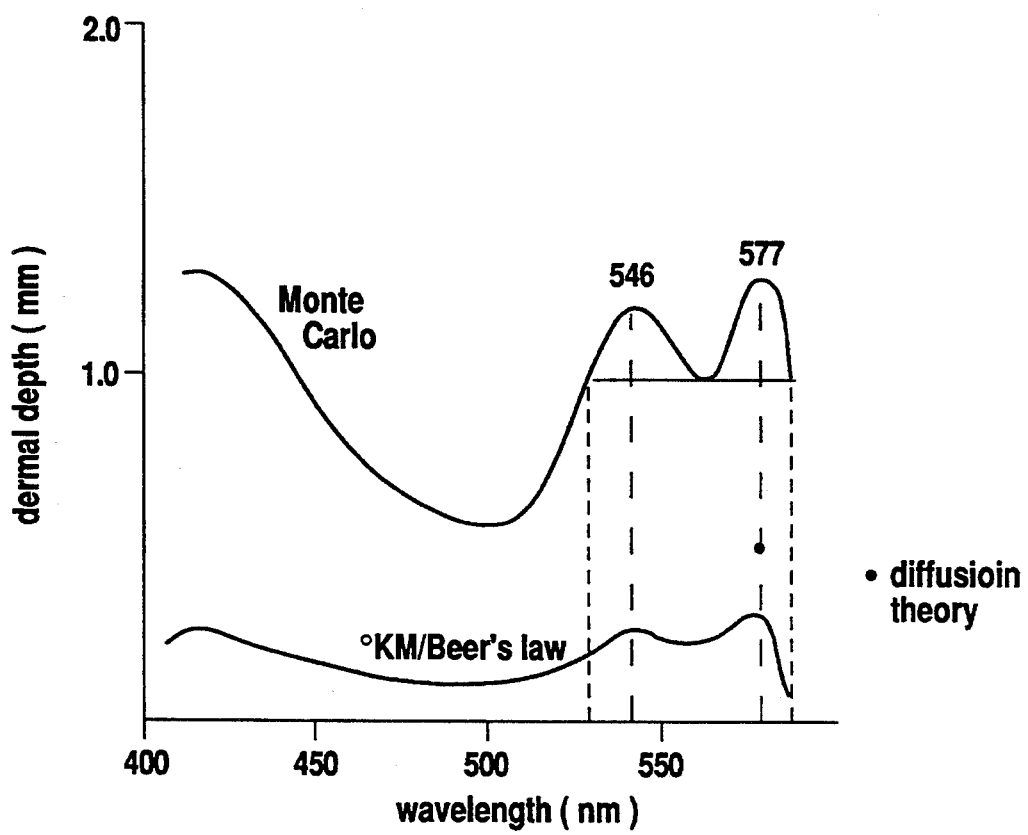
FIG. 12 is the maximum dermal depth as a function of wavelength where the heat production at the top of the blood vessel is larger than at the epidermal-dermal junction using Monte Carlo and Kubelka-Munk theories.

FIG. 12 is the maximum dermal depth as a function of wavelength where the heat production at the top of the blood vessel is larger than at the epidermal-dermal junction using Monte Carlo and Kubelka-Munk theories. Different wavelengths from 525 to 585 nm may produce blood vessel coagulation in depths of interest; however, the wavelengths in the vicinity of 546 and 577 nm may be more suitable. Irradiation containing the band of wavelengths around the 546 nm peak produces a higher epidermal temperature increase than an equal irradiance containing the band of wavelengths around 577 nm peak (for the case of the Arc lamp). However, surface cooling will reduce the epidermal temperatures such that the epidermal temperature increase due to the wavelengths around the 546 peak becomes closer to that of the peak around 577 nm. The two peaks of interest in the light source and their interaction is explained in the next section.

SYSTEM FOR CONTROL OF SKIN TEMPERATURE

Figure 13:
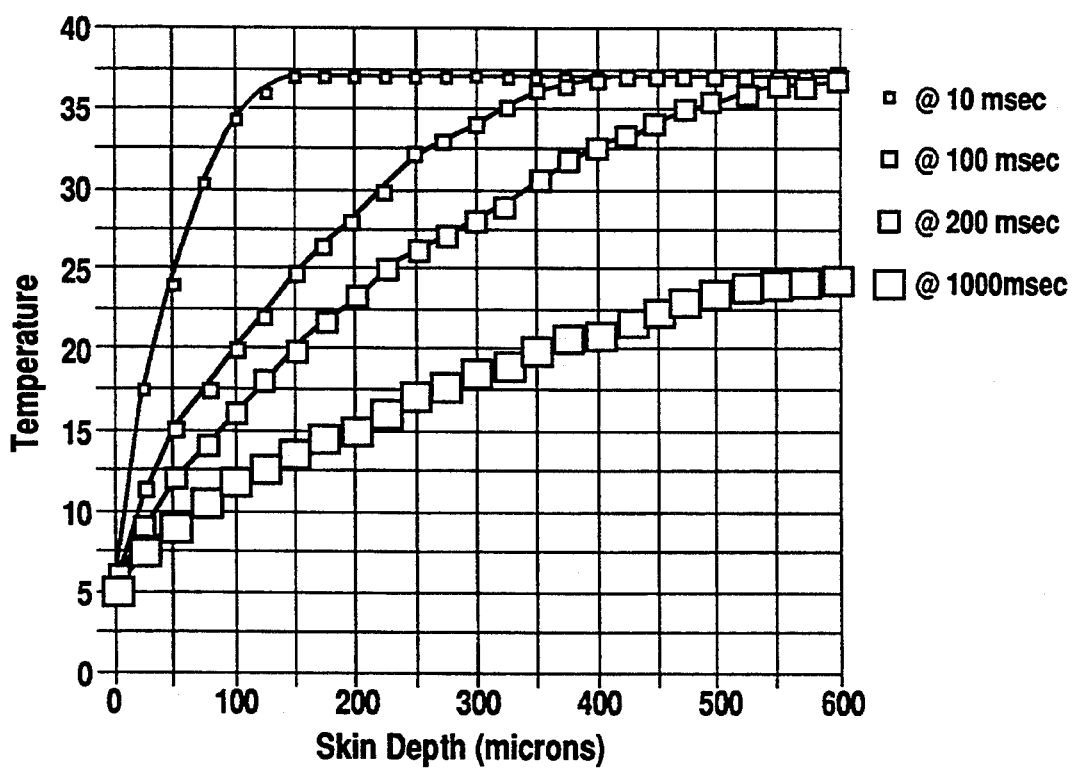
FIG. 13 is a graphical illustration of skin temperature as a function of depth for cooling at various rates.

The temperature cooling system provided by the present invention is a pulsed cooling system with capability of dropping the skin surface temperature to 5° C. in about 100 milliseconds. The computed temperature response of the skin for a fixed surface temperature of 5° C., and the onset of light irradiation after 100 ms is shown in FIG. 13. Blood vessels at a depth of 100 microns are cooled to 20° C. at the onset of light irradiation.

As the surface temperature of the skin is rapidly cooled to approximately 5° C., temperatures in the epidermis and upper dermis will be lower than the normal skin temperature. The epidermal temperatures at the beginning of irradiation are lower than temperatures when cooling is omitted. At the end of an irradiation pulse of 10-50 milliseconds, blood vessels are coagulated when temperatures reach 65° to 75° C. With surface cooling corresponding peak temperatures at the epidermal-dermal junction are expected to be in the range of 40° to 50° C. Since rapid cooling of the skin creates lower blood vessel temperatures in the anterior vessels than the posterior vessels; the temperature of the vessels during light irradiation will be more uniform with depth than the present laser treatment.

Due to its thermal properties, sapphire or diamond are particularly suitable material for this application. They are transparent to visible light, allowing the laser beam to pass through and at the same time they possess high thermal conductivities (25 W/m °K and higher) or higher, allowing rapid transfer of heat which produces a lower temperature that advance to the front of the lens (and to the skin surface if the sapphire lens is touching the skin) while irradiation is being performed. Prior to the application, the skin surface must be exposed to saline or transparent ointments with high heat conductivity for better heat coupling efficiencies. The freon or $CO_2$ flow is controlled by a computer monitoring feedback system to keep the skin temperature at or above 5° C.

The system provided by the present invention offers numerous advantages over the prior art systems. The estimated manufacturing cost of the proposed system is much lower than a laser dye system. The lower manufacturing cost may reduce the treatment cost dramatically.

Another advantage of the proposed system is the ability to control the treatment by changing the rate of cooling, irradiation time and the spectrum of the irradiation light. The maximum temperatures for the dermis and blood vessels can be adjusted by changing the treatment protocol.

The superficial blood vessels may be "shut down" by the rapid cooling; as a result, the cooling system may initially shut down the superficial blood vessels so that the light would coagulate the deeper vessels. The proposed delivery system allows an increase in the total light energy delivered, so more abnormal blood vessels can be destroyed while preserving the epidermis and the epidermal-dermal junction. In other words, more lightening of the PWS lesion may be obtained with less risk of scarring.

The system will be easy to use and can be moved freely on the skin keeping the skin at the same relative distance from the lenses.

Presently used lasers are not power efficient. The efficiency of some lasers used in this application may be as low as 0.01%. The Arc lamp is a much more efficient system. Total light generation capability of the Arc lamp is in the order of 40-60%. In this application only 9% of the light is used for the treatment which makes this system more efficient than the dye lasers. A reasonably sized portable system may be feasible if there is a need for such device. Finally, due to the large area cooling system, the pain may be reduced.

While the foregoing discussion of the invention contains many specificities, these should not be construed as limiting the scope of the invention, but rather as merely providing illustrations of exemplary embodiments of the invention. Many other variations and modifications of the invention will be apparent to those of skill in the art without departing from the spirit and the scope of the invention as defined by the appended claims and their equivalents.

What is claimed is:

1. An optical system for treating vascular lesions, comprising:
    irradiating means for irradiating skin with electromagnetic radiation;
    monitoring means coupled to said irradiating means for monitoring absorption of said radiation by said skin;
    controlling means coupled to said monitoring means and said irradiating means for controlling the operation of said irradiating means to deliver a predetermined dose of radiation to said skin; and
    cooling means coupled to said irradiating means for cooling the surface of said skin, said cooling means comprising:

a lens having one side in contact with said skin, wherein said lens is comprised of a material that is transparent to visible light and has a high thermal conductivity; and means for circulating a cooling gas to contact with said lens on the side not in contact with said skin.

2. The system of claim 1, wherein said irradiating means comprises an arc lamp.

3. The system of claim 2, wherein said monitoring means comprises means for measuring the time of absorption of radiation.

4. The system of claim 2, wherein said monitoring means comprises means for measuring the reflection of radiation from the skin.

5. The system of claim 1, wherein said cooling gas comprises freon.

6. The system of claim 1, wherein said cooling gas comprises carbon dioxide.

7. The system of claim 1, wherein said lens material is sapphire.

8. The system of claim 1, wherein said lens material is diamond.

* * * * *